United States Patent
Sereno et al.

(10) Patent No.: US 10,106,493 B2
(45) Date of Patent: Oct. 23, 2018

(54) N-HYDROXYBENZAMIDES AS HDAC INHIBITORS FOR THE TREATMENT OF PARASITIC DISEASES

(71) Applicants: INSTITUT DE RECHERCHE POUR LE DEVELOPPEMENT (I.R.D.), Marseilles (FR); UNIVERSITE DE MONTPELLIER, Montpellier (FR); CENTRE NATIONAL DE LA RECHERCHE SCIENTIFIQUE, Paris (FR)

(72) Inventors: Denis Sereno, Poussan (FR); Gilles Labesse, Montpellier (FR); Jean-Francois Alexandre Guichou, Uchaud (FR); Corinne Loeuillet, Goncelin (FR); Deborah Isabelle Garcia, Gouzigues (FR); Stephane Delbecq, Montpellier (FR)

(73) Assignees: INSTITUT DE RECHERCHE POUR LE DEVELOPPEMENT (I.R.D.), Marseilles (FR); UNIVERSITE DE MONTPELLIER, Montpellier (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 14/906,206

(22) PCT Filed: Jul. 17, 2014

(86) PCT No.: PCT/EP2014/065449
§ 371 (c)(1),
(2) Date: Jan. 19, 2016

(87) PCT Pub. No.: WO2015/007870
PCT Pub. Date: Jan. 22, 2015

(65) Prior Publication Data
US 2016/0168084 A1 Jun. 16, 2016

(30) Foreign Application Priority Data

Jul. 18, 2013 (EP) .................................. 13177129

(51) Int. Cl.
| | | |
|---|---|---|
| *C07C 259/06* | (2006.01) | |
| *C07C 259/10* | (2006.01) | |
| *C07C 311/19* | (2006.01) | |
| *C07C 311/21* | (2006.01) | |
| *C07D 277/30* | (2006.01) | |

(52) U.S. Cl.
CPC .......... *C07C 259/06* (2013.01); *C07C 259/10* (2013.01); *C07C 311/19* (2013.01); *C07C 311/21* (2013.01); *C07D 277/30* (2013.01)

(58) Field of Classification Search
CPC ... C07C 259/06; C07C 259/10; C07C 311/19; C07C 311/21; C07D 277/30
See application file for complete search history.

(56) References Cited

U.S. PATENT DOCUMENTS

| | | | |
|---|---|---|---|
| 2002/0172967 A1 | 11/2002 | Gadek et al. | |
| 2003/0013757 A1 | 1/2003 | Leser-Reiff et al. | |
| 2006/0100285 A1* | 5/2006 | Pinori .................... | A61K 31/16 514/575 |
| 2006/0252834 A1 | 11/2006 | Rho et al. | |

(Continued)

FOREIGN PATENT DOCUMENTS

| | | |
|---|---|---|
| WO | 2004/063146 A1 | 7/2004 |
| WO | 2006/017214 A2 | 2/2006 |

(Continued)

OTHER PUBLICATIONS

"Derivative" definition: On-line Medical Dictionary (Jul. 7, 2005) p. 1-3.*

(Continued)

*Primary Examiner* — Valerie Rodriguez-Garcia
(74) *Attorney, Agent, or Firm* — Young & Thompson

(57) ABSTRACT

Compounds of formula

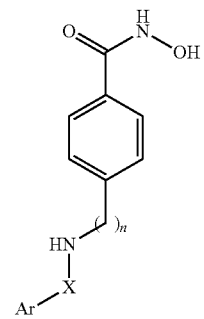

wherein n is 0, 1 or 2; X is

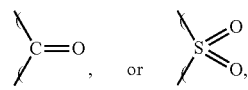

and Ar is a benzyl substituted at the meta position by a $C_1$ to $C_8$ alkoxy group, or a pharmaceutically acceptable salt thereof, for treating, preventing or inhibiting a parasitic disease, such as toxoplasmosis, in a subject are provided. Methods for preparing the compounds are also presented.

11 Claims, 6 Drawing Sheets

(56) References Cited

U.S. PATENT DOCUMENTS

2007/0066646 A1    3/2007  Clauzel et al.

FOREIGN PATENT DOCUMENTS

WO     2012/019772 A1    2/2012
WO     2013/057186 A1    4/2013

OTHER PUBLICATIONS

European Search Report dated Oct. 2, 2013, in corresponding EP Application 13 17 7129.
International Search Report dated Oct. 27, 2014 in corresponding PCT application.
Maeda Taishi et al: "Potent histone deacetylase inhibitors: N-hydroxybenzamides with antitumor activities", Bioorganic & Medicinal Chemistry, Pergamon, GB, vol. 12, No. 16, Jul. 7, 2004 (Jul. 7, 2004), pp. 4351-4360, XP008122886, ISSN: 0968-0896.
Jie Mao et al: "Design, synthesis and preliminary biological evaluation of N-hydroxy-4-(3-phenylpropanamido) benzamide (HPPB) derivatives as novel histone deacetylase inhibitors", European Journal of Medicinal Chemistry, vol. 44, No. 11, Nov. 1, 2999 (2999-11-91), pp. 4479-4476, XP9SS9S1534, ISSN: 9223-5234.

\* cited by examiner

N-HYDROXYBENZAMIDES AS HDAC INHIBITORS FOR THE TREATMENT OF PARASITIC DISEASES

FIELD OF THE INVENTION

The present invention relates to new compounds for treating, preventing or inhibiting a parasitic disease, preferably toxoplasmosis in a subject, the method for preparing thereof.

BACKGROUND

Toxoplasmosis is caused by parasite *Toxoplasma gondii*, which is transmitted through meat containing *T. gondii* cysts or water containing oocyst from feline feces. *T. gondii* infection in human can make eye and brain injuries, systemic illness and even death. *Toxoplasma gondii* can exist in two cellular stages: a rapidly proliferating tachyzoïte form, and a latent encysted bradyzoite form, which remains in the body for the duration of the lifetime of the host, maintaining the risk of recurrence. There are currently no effective treatments against the bradyzoïte form. Available medicaments which target the tachyzoïte form, such as pyrimethamine and sulfadiazine, present also high toxicity and hypersensitivity.

An international application PCT/EP2011/004055 discloses that hydroxybenzamide has a good antiparasitic activity, but it presents only a moderate activity against intracellular form of *Leishmania*.

Document US2003/013757 A1 discloses aromatic dicarboxylic acid derivatives,
including a compound of formula:

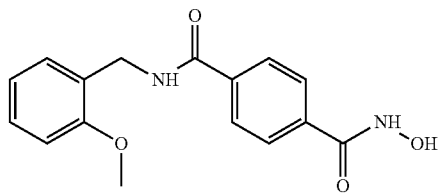 [SMILES: COc1ccccc1CNC(=O)c1ccc(C(=O)NO)cc1]

with anti-tumor cell-proliferation activity.

Recently, several Histone deacetylases (HDAC) inhibitors with anti *T. gondii* potential were characterized (Strobl et al., *J Parasitol.* 2007; 93(3):694-700; Bougdour et al., *Exp Med.* 2009, 206(4):953-66; Maubon et al., *Antimicrob Agents Chemother.* 2010, 54(11):4843-50). Histone deacetylases play key roles in epigenetic regulation and in various intracellular processes (Tang et al., Clin Sci (Lond). 2013. 124 (11): 651-662. They act through the modification of histone and non-histone proteins leading to transcription repression. Increasing amounts of evidences indicate that histone deacetylase are promising drug target in various parasitic born diseases (Andrews et al., *Immunol Cell Biol.* 2012, 90(1):66-77). It was observed that apicidin, a fungal metabolite with nanomolar HDAC inhibitory activity, express a strong antiparasitic activity against *Plasmodium falciparum* (Darkin-Rattray et al., *Proc Natl Acad Sci USA.* 1996, 93(23):13143-7). Additionally, some classes of HDAC inhibitor express a broader spectrum of antiparasitic activity acting on *Plasmodium falciparum* and *Leishmania* (Mai et al., *Antimicrob. Agents Chemother.* 2004, 48:1435-1436). The *Toxoplasma gondii* genome contains five putative class-I/II HDAC homologues (Toxobd.org). Among them, TgHDAC3 is a part of a large multi-protein complex termed the *T. gondii* co-repressor complex, whose deacetylase activity is sensitive to HDAC inhibitors. *T. gondii* HDACs have also been shown to function in stage-specific gene regulation during the differentiation from tachyzoites to bradyzoites (Saksouk et al., *Mol Cell Biol* 2005, 25: 10301-10314). Recently, novel derivatives of the tetrapeptide FR235222 with inhibitory *T. gondii* activity have been synthesized (Maubon et al., 2010).

However unfortunately, HDAC inhibitors known in prior art need to be used in high concentration to inhibit parasite growth and additionally most of HDAC inhibitors show little selectivity for the intracellular stage of parasites compared with their selectivity for human cells or for specific HDAC. This low specificity, lack of selectivity and/or in vivo activity of HDAC inhibitors have therefore greatly hampered the development of an HDAC inhibitor based *T. gondii* therapy.

Therefore, the development of new medicaments with a high selectivity index against *T. gondii* remains challenging and is urgently required.

SUMMARY OF THE INVENTION

One of the objectives of the present invention is to provide a family of new compounds presenting anti-parasitic activity, in particular in infected individuals and more particularly in infected drug resistant individuals.

The Inventors have synthesised and tested a family of new compounds which are derivatives of hydroxybenzamide, and observed that they present an anti-parasitic activity by inhibiting HDAC activity. The Inventors observed a potent and specific inhibitory activity of synthesised compounds on specific HDACs. Moreover, these new compounds in vitro inhibit *T. gondii* intracellular tachyzoïte stage proliferation.

The present invention is to provide compounds of formula (I):

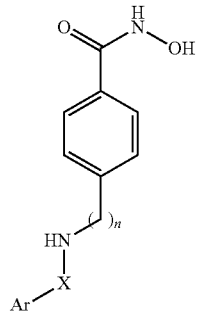

wherein:
n is a natural number chosen from 0, 1 and 2,
X is chosen from

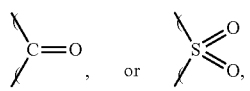

Ar is an aryl, preferably a phenyl, or an arylalkyl, preferably a benzyl, said aryl or arylalkyl being substituted by a halogen, preferably a fluor atom, a thiazolyl, or a group chosen from: —R$_1$, —OR$_1$, —R$_2$—O—R$_1$, wherein R$_1$ represents a C$_1$-C$_8$-alkyl, which is eventually substituted by a halogen, preferably a fluor atom or a thiazolyl, R$_2$ represents a C$_1$-C$_8$ alkylene group eventually substituted by a halogen, preferably a fluor atom or a thiazolyl, or a pharmaceutically acceptable salt thereof.

The term "aryl" refers to a 6- to 18-membered monocyclic, bicyclic, tricyclic, or polycyclic aromatic hydrocarbon ring system. Examples of an aryl group include phenyl, naphthyl, pyrenyl, anthracyl, quinolyl, and isoquinolyl.

The term "arylalkyl" refers to an aryl wherein at least a hydrogen is substituted by a C$_1$-C$_8$-alkyl. One examples of an arylalkyl can be preferably a benzyl.

The term "C$_1$-C$_8$ alkyl" denotes a straight or branched chain hydrocarbon group with 1 to 8 carbon atoms, especially with 1 to 6 carbon atoms, more especially with 1 to 4 carbon atoms. Examples of such groups are methyl, ethyl, propyl, isopropyl, butyl, isobutyl, sec-butyl, tert-butyl, pentyl, isopentyl, neopentyl, tert-pentyl, hexyl, isohexyl, 1,1-dimethylbutyl, 2,2-dimethylbutyl, 3,3-dimethylbutyl and 2-ethylbutyl.

The term "pharmaceutically acceptable salt" refers to salt forms that are pharmacologically acceptable and substantially non-toxic to the subject being treated with the compound of the invention. The pharmaceutically acceptable salt forms of the compound of formula (I) may be prepared according to methods well known in the art.

Pharmaceutically acceptable salts can be salts formed with pharmaceutically acceptable organic or inorganic acids.

Organic acids can be chosen from the list comprising acetic acid, citric acid, tartaric acid, methanesulfonic acid, maleic acid, fumaric acid, benzoic acid, succinic acid, lactic acid, gluconic acid, phenylsulfonic acid, p-toluenesulfonic acid, or any mixture of these acids.

Inorganic acids can be chosen from the list comprising hydrochloric acid, hydrobromic acid, hydroiodic acid, sulfuric acid, phosphoric acid, or any mixture of the these acids.

Examples of corresponding acid addition salts are acetate, malate, fumarate, benzoate, succinate, lactate, citrate, gluconate, methanesulfate, phenylsulfate, p-toluenesulfate, hydrochloride, hydrobromide, hydroiodide, sulfate or bisulfate, phosphate or biphosphate, tartrate.

DETAILED DESCRIPTION OF THE INVENTION

In a preferred embodiment, the invention concerns acetate of a compound of formula (I).

In a particular embodiment, the invention concerns a compound of formula (I), wherein Ar is a phenyl or a benzyl, said phenyl of benzyl being substituted at the meta, para or ortho position.

"A phenyl of benzyl substituted at the ortho position" refers to a phenyl of a benzyl wherein the first substituent and the second substituent are respectively at the position 1 and 2 of the benzene.

"A phenyl of benzyl substituted at the meta position" refers to a phenyl of a benzyl wherein the first substituent and the second substituent are respectively at the position 1 and 3 of the benzene.

"A phenyl of benzyl substituted at the para position" refers to a phenyl of a benzyl wherein the first substituent and the second substituent are respectively at the position 1 and 4 of the benzene.

In a particular embodiment, the invention concerns a compound of formula (I), wherein Ar is chosen from i) a phenyl substituted at the meta-, para- or ortho-position by a fluor ou a thiazolyl, or ii) a benzyl substituted at the meta-, para- or ortho-position by an C1 to C4 alkoxy group, preferably a methoxy group.

In a more particular embodiment, the invention concerns a compound of formula (I), wherein n is a natural number chosen from 0 or 1

X is chosen from

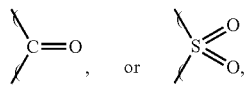

Ar is:

i) a phenyl substituted at the meta-, para- or ortho-position by a fluor ou a thiazolyl, or ii) a benzyl substituted at the meta-, para- or ortho-position by an C1 to C4 alkoxy group, preferably a methoxy group.

In another particular embodiment, the invention concerns a compound of formula (I), wherein:

n is a natural number chosen from 0, 1 and 2,

X is chosen from

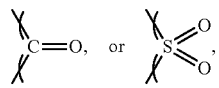

Ar is a benzyl substituted at the meta-position by a methoxy group. said compound corresponding to formula (Ia):

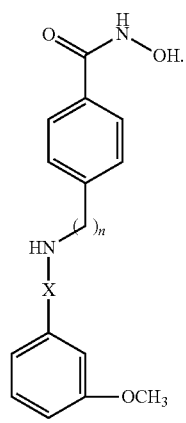

In a more particular embodiment, the invention concerns the compound of formula (Ia), wherein n is 0 and X is

said compound corresponding to formula (Ia1):

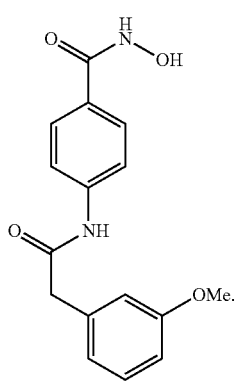
(363)

In another more particular embodiment, the invention concerns the compounds of formula (Ia), wherein n is 1 and X is

said compound corresponding to formula (Ia2):

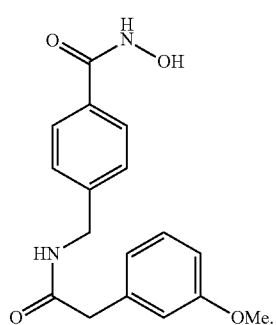
(362)

In another particular embodiment, the invention concerns a compound of formula (I), wherein:
n is a natural number chosen from 0, 1 and 2,
X is chosen from

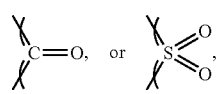

Ar is a phenyl substituted at the meta-position by a fluor (compounds 345, 349, 350, 351), said compound corresponding to formula (I)b:

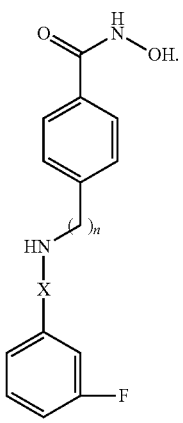

In a more particular embodiment, the invention concerns a compound of formula (Ib), wherein n is 1 and X is

said compound corresponding to formula (Ib1)

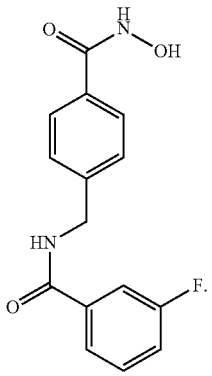
(345)

In another more particular embodiment, the invention concerns a compound of formula (Ib), wherein n is 0 and X is

said compound corresponding to formula (Ib2):

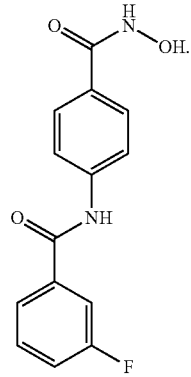
(349)

In another more particular embodiment, the invention concerns a compound of formula (Ib), wherein n is 1 and X is

said compound corresponding to formula (Ib3):

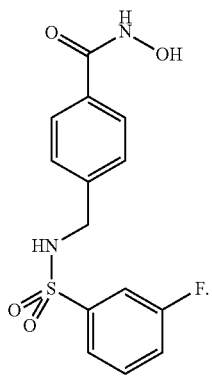
(350)

In another more particular embodiment, the invention concerns a compound of formula (Ib), wherein n is 0 and X is

said compound corresponding to formula (Ib4):

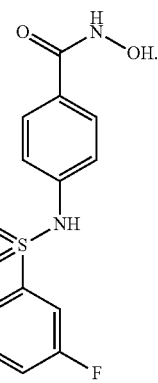
(351)

In another particular embodiment, the invention concerns a compound of formula (I), wherein:
n is a natural number chosen from 0, 1 and 2,
X is chosen from

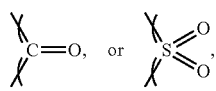

Ar is a phenyl substituted at para position by

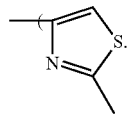

(compounds 360, 361) said compound corresponding to formula (Ic):

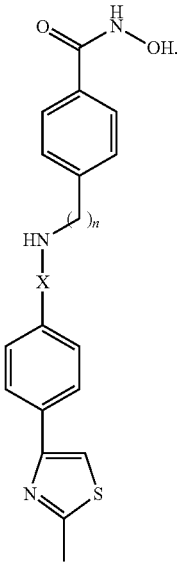

In a more particular embodiment, the invention concerns a compound of formula (Ic), wherein n is 1 and X is

said compound corresponding to formula (Ic1)

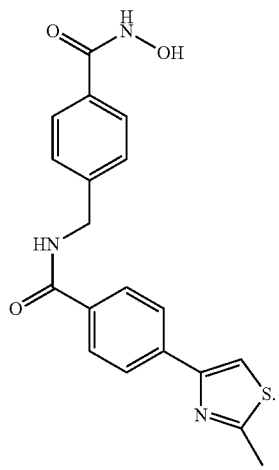

(360)

In another more particular embodiment, the invention concerns a compound of formula (Ic), wherein n is 0 and X is

said compound corresponding to formula (Ic2):

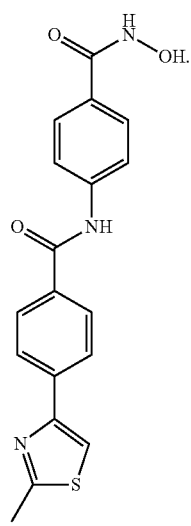

(361)

The present invention concerns also an above-defined compound of formula (I), preferably a compound of formula (Ia), (Ib), (Ic), more preferably a compound of formula (Ia1), (Ia2), (Ib1), (Ib2), (Ib3), (Ib4), (Ic1), (Ic2), for its use as a pharmaceutical drug.

More preferably, the present invention concerns an above-defined compound of formula (I), preferably a compound of formula (Ia), (Ib), (Ic), more preferably a compound of formula (Ia1), (Ia2), (Ib1), (Ib2), (Ib3), (Ib4), (Ic1), (Ic2), for its use as a pharmaceutical drug for treating, inhibiting or preventing a parasitic disease, preferably a protozoan parasitic disease in a subject.

Even more preferably, the present invention concerns a compound of formula (I) or (I'), for its use as a pharmaceutical drug for treating, inhibiting or preventing a parasitic disease, preferably a protozoan parasitic disease in a drug-resistant subject.

The term "subject" refers to a mammalian including human, cat or dog.

The term "drug-resistant subject" or "drug resistant individual" is a subject including human, cat or dog suffering a disease and taking a drug in doses equal to or higher than those usually recommended but within the limits of tolerance with no or little improvement of his state of health.

In general, drug resistance is "the ability of a parasite strain to survive and/or multiply despite the administration and absorption of a drug in doses equal to or higher than those usually recommended but within the limits of tolerance of the subject".

In a particular embodiment drug resistant subjects or drug resistant patients are patients resistant to one or several drugs selected from anti-parasitic drugs, in particular a drug selected from miltefosin, meglumine, antimoniate, sodium stibogluconate, amphotericin B, benzimidazol, nifurtimox, paromomycin, pentamidin melarsoprol, difluoromethylornithin, or a combination thereof.

Said parasitic disease is chosen from toxoplasmosis, leishmaniasis, or trypanosomiasis, preferably a disease caused by a protozoan parasite of the family of the Trypanosomatidae selected from the genus *Trypanosoma* or the genus *Leishmania*, or the parasite *Toxoplasma gondii*.

Said parasitic disease is chosen from toxoplasmosis, leishmaniasis, babesiosis or piroplasmosis or trypanosomiasis, preferably a disease caused by a protozoan parasite of the family of the Trypanosomatidae selected from the genus *Trypanosoma* or the genus *Leishmania*, or the parasite *Toxoplasma gondii*.

In a particular embodiment, said parasitic disease is babesiosis or piroplasmosis.

In a particular embodiment, the present invention concerns a compound of formula (Ia1), (Ib1), or (Ic1) for its use as a pharmaceutical drug for treating toxoplasmosis.

In a more particular embodiment, the present invention concerns a compound of formula (Ib1) for its use as a pharmaceutical drug for treating toxoplasmosis and leshmaniasis.

Another subject-matter of the present invention concerns a pharmaceutical composition comprising a compound of formula (I) or a pharmaceutical acceptable salt thereof, and a pharmaceutical acceptable excipient.

Said excipient can be any conventional pharmaceutical acceptable excipient. They are non-API substances such as disintegrators, binders, fillers, bulking agent and lubricants used in formulating pharmaceutical products. They are generally non-toxic for administering to humans.

The above defined compound or the composition is administrated to a subject in need thereof in a therapeutically effective amount.

The term "therapeutically effective amount" refers to an amount which prevents, inhibits, suppresses or reduces the amount of parasite in a subject, for example the number of *T. gondii* in tachyzoïte form or bradyzoïte form, or both in a subject, or the number of *Leishmania* or *Trypanosoma* amastigotes, promastigotes, or both in a subject, as compared to a control. The therapeutically effective amount may be determined by conventional methods known in the art.

The term "therapeutically effective amount" refers to an amount which prevents, inhibits, suppresses or reduces the amount of parasite in a subject, for example the number of *babesia* (or *nuttaliia*), in particular of *Babesia microti* or *Babesia divergens*.

In a preferred embodiment, a therapeutically effective amount of a compound of formula (I) can be administered, as an example, at a unitary amount from 1 mg/KG/day to 500 mg/kg/day. However, one skilled in the art will know that this standard amount could be influenced by certain factors, such as the severity of the disease or disorder, previous treatment, the general health and/or age of the subject accepting the treatment, and other disease present.

The present invention is also to provide a composition comprising a compound of formula (I), or a pharmaceutically acceptable salt thereof, and at least a conventional anti-parasitic compound.

Said conventional anti-parasitic compound is selected from the group comprising: miltefosin, antimony based drugs, like meglumine antimoniate or sodium stibogluconate, amphotericin B, benzimidazol, nifurtimox, paromomycin, pentamidin and its derivatives, arsenic derivatives, melarsoprol and difluoromethylornithin.

In another embodiment, said conventional anti-parasitic compound is selected from the group comprising: miltefosin, antimony based drugs, like meglumine antimoniate or sodium stibogluconate, amphotericin B, benzimidazol, nifurtimox, paromomycin, pentamidin and its derivatives, arsenic derivatives, melarsoprol and difluoromethylornithin, clindamycin, quinine, atovaquone, azithromycin.

In a particular embodiment, the present invention concerns a composition comprising a compound of formula (Ia1), (Ib1), or (Ic1) or a pharmaceutically acceptable salt thereof, and at least a conventional anti-parasitic compound selected from the group comprising: miltefosin, antimony based drugs, like meglumine antimoniate or sodium stibogluconate, amphotericin B, benzimidazol, nifurtimox, paromomycin, pentamidin and its derivatives, arsenic derivatives, melarsoprol and difluoromethylornithin.

In another particular embodiment, the present invention concerns a composition comprising a compound of formula (Ia1), (Ib1), or (Ic1) or a pharmaceutically acceptable salt thereof, and at least a conventional anti-parasitic compound selected from the group comprising: miltefosin, antimony based drugs, like meglumine antimoniate or sodium stibogluconate, amphotericin B, benzimidazol, nifurtimox, paromomycin, pentamidin and its derivatives, arsenic derivatives, melarsoprol and difluoromethylornithin, clindamycin, quinine, atovaquone, azithromycin The present invention provides also a product comprising:
a compound of formula (I), or a pharmaceutically acceptable salt thereof,
at least a conventional anti-parasitic compound,
as a combination for the simultaneous, separate use or successive administration for the treatment and/or the prevention of a parasitic disease.

In a particular embodiment, the present invention concerns a product comprising:
a compound of formula (Ia1), (Ib1), or (Ic1) or a pharmaceutically acceptable salt thereof, or a pharmaceutically acceptable salt thereof,
at least a conventional anti-parasitic compound selected from the group comprising: miltefosin, antimony based drugs, like meglumine antimoniate or sodium stibogluconate, amphotericin B, benzimidazol, nifurtimox, paromomycin, pentamidin and its derivatives, arsenic derivatives, melarsoprol and difluoromethylornithin, as a combination for the simultaneous, separate use or successive administration for the treatment and/or the prevention of a parasitic disease.

The above defined pharmaceutical compositions or separate parts of the above defined products could be formulated as tablets, pills, capsules, liquids, gels, syrups, slurries or suspensions.

The administration of the above defined pharmaceutical compositions or products could be carried out by oral, rectal, nasal, topical (including buccal and sublingual), parenteral (including subcutaneous, intramuscular, intravenous and intradermal) or intralesional route.

As intended herein "intralesional" means that the administration of the compound of formula (I) is carried out at the sites of parasite-caused skin lesions of patients.

The present invention provides also a method for treating, inhibiting, or preventing a parasitic disease chosen from toxoplasmosis, a leishmaniasis or trypanosomiasis, more preferably a disease caused by a protozoan parasite of the family of the Trypanosomatidae selected from the genus *Trypanosoma* or the genus *Leishmania*, or the parasite *Toxoplasma gondii*, in a subject in need thereof comprising administering to said subject at least a therapeutically effective amount of a compound of formula (I), preferably a compound of formula (Ia), (Ib), (Ic), more preferably a compound of formula (Ia1), (Ia2), (Ib1), (Ib2), (Ib3), (Ib4), (Ic1), (Ic2).

In a preferred embodiment, the invention provides also a method for treating, inhibiting, or preventing babesiosis, more preferably a disease caused by a protozoan parasite of the family of the *Babesia* genus selected from *Babesia microti* and *Babesia divergens* in a subject in need thereof comprising administering to said subject at least a therapeutically effective amount of a compound of formula (I) or (I'), preferably a compound of formula (Ia), (Ib), (Ic), more preferably a compound of formula (Ia1), (Ia2), (Ib1), (Ib2), (Ib3), (Ib4), (Ic1), (Ic2).

In a more preferred embodiment, the invention provides also a compound of formula (I) or (I'), preferably a compound of formula (Ia), (Ib), (Ic), more preferably a compound of formula (Ia1), (Ia2), (Ib1), (Ib2), (Ib3), (Ib4), (Ic1), (Ic2) for treating, inhibiting, or preventing babesiosis, more preferably a disease caused by a protozoan parasite of the family of the *Babesia* genus selected from *Babesia microti* and *Babesia divergens* in a subject in need thereof.

Another subject-matter of the present invention is a method for preparing a compound of formula (I).

Said method comprises the following steps:
(i) the reaction between a compound of formula II

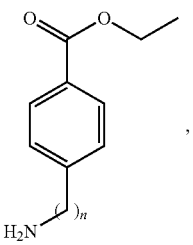

wherein n is a natural number chosen from 0, 1 and 2, with a compound of formula III: Ar—X—Cl, wherein X is chosen from

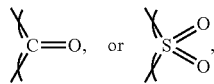

Ar is an aryl, preferably a phenyl, or an arylalkyl, preferably a benzyl, said aryl or arylalkyl being substituted by a halogen, preferably a fluor atom, a thiazolyl, or a group chosen from: —R₁, —OR₁, —R₂—O—R₁, wherein R₁ represents a C₁-C₈-alkyl, which is eventually substituted by a halogen, preferably a fluor atom or a thiazolyl, R₂ represents a C₁-C₈ alkylene group eventually substituted by a halogen, preferably a fluor atom or a thiazolyl, to obtain a compound of formula IV

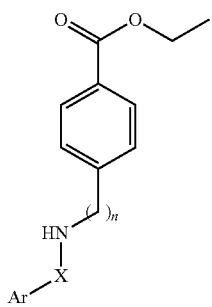

wherein:
n is a natural number chosen from 0, 1 and 2,
X is chosen from

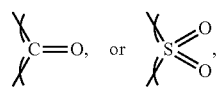

Ar is an aryl, preferably a phenyl, or an arylalkyl, preferably a benzyl, said aryl or arylalkyl being substituted by a halogen, preferably a fluor atom, a thiazolyl, or a group chosen from: —R₁, —OR₁, —R₂—O—R₁, wherein R₁ represents a C₁-C₈-alkyl, which is eventually substituted by a halogen, preferably a fluor atom or a thiazolyl, R₂ represents a C₁-C₈ alkylene group eventually substituted by a halogen, preferably a fluor atom or a thiazolyl, (ii) the reaction between the compound of formula IV and a base to obtain a compound of formula V

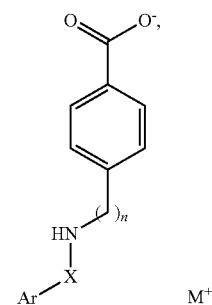

wherein n, X and Ar respectively has the same definition of that for formula IV, said compound of formula V is eventually acidified,
and M⁺ represents a metallic cation, preferably Na⁺, K⁺, or Li+;
(iii) the reaction between the compound of formula V and hydroxylamine to obtain the compound of formula I.

A base used in the step (ii) of the present method can be LiOH, NaOH, or KOH.

A compound of formula V of the present method can be acidified by an acid, preferably HCl.

In a particular embodiment the invention concerns compound of formula (I) which is a compound of formula (I') of formula:

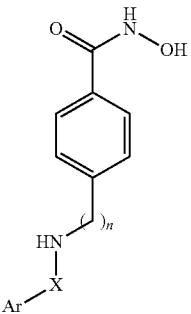

wherein:
n is a natural number chosen from 0, 1 and 2,
X is chosen from

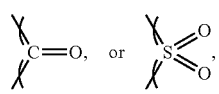

Ar is an aryl, preferably a phenyl, or an arylalkyl, preferably a benzyl, said aryl or arylalkyl being substituted by a halogen, which is a fluor atom, a thiazolyl, or a group chosen from: —OR₁ in meta position, —R₂—O—R₁, wherein R₁ represents a C₁-C₈-alkyl, which is eventually substituted by a halogen, preferably a fluor atom or a thiazolyl, R₂ represents a C₁-C₈ alkylene group eventually substituted by a halogen, preferably a fluor atom or a thiazolyl, or a pharmaceutically acceptable salt thereof.

Advantageously, the invention relates to compound of formula (I'), wherein Ar is chosen from
i) a phenyl substituted at the meta-, para- or ortho-position by a fluor or a thiazolyl, or
ii) a benzyl substituted at the meta-position by an C1 to C4 alkoxy group, preferably a methoxy group.

More advantageously, the inventions concerns compound of formula (I'), wherein
n is a natural number chosen from 0, 1 and 2,
X is chosen from

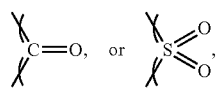

Ar is a benzyl substituted at the meta-position by a methoxy group. said compound corresponding to formula (Ia):

[Structure: 4-(hydroxycarbamoyl)phenyl-CH2-(n)-NH-X-phenyl(3-OCH3)]

and even more advantageously, compound of formula (Ia), wherein either n is 0 and X is $$\overset{\displaystyle\diagup}{\underset{\displaystyle\diagdown}{C}}=O,$$

said compound corresponding to formula (Ia1), or wherein n is 1 and X is $$\overset{\displaystyle\diagup}{\underset{\displaystyle\diagdown}{C}}=O,$$

said compound corresponding to formula (Ia2).
The present invention relates to compound of formula (I'), wherein
   n is a natural number chosen from 0, 1 and 2,
   X is chosen from $$\overset{\displaystyle\diagup}{\underset{\displaystyle\diagdown}{C}}=O, \quad \text{or} \quad \overset{\displaystyle\diagup}{\underset{\displaystyle\diagdown}{S}}\overset{\displaystyle=O}{\underset{\displaystyle=O}{}},$$

Ar is a phenyl substituted at the meta-position by a fluor, said compound corresponding to formula (Ib):

[Structure: 4-(hydroxycarbamoyl)phenyl-CH2-(n)-NH-X-phenyl(3-F)]

Advantageously, the present invention concerns compound of formula (Ib), wherein either n is 1 and X is $$\overset{\displaystyle\diagup}{\underset{\displaystyle\diagdown}{C}}=O,$$

said compound corresponding to formula (Ib1), or wherein n is 0 and X is $$\overset{\displaystyle\diagup}{\underset{\displaystyle\diagdown}{C}}=O,$$

said compound corresponding to formula (Ib2), or wherein n is 1 and X is $$\overset{\displaystyle\diagup}{\underset{\displaystyle\diagdown}{S}}\overset{\displaystyle=O}{\underset{\displaystyle=O}{}},$$

said compound corresponding to formula (Ib3), or wherein n is 0 and X is $$\overset{\displaystyle\diagup}{\underset{\displaystyle\diagdown}{S}}\overset{\displaystyle=O}{\underset{\displaystyle=O}{}},$$

said compound corresponding to formula (Ib4).
In a particular embodiment, the present invention concerns compound of formula (I'), wherein
   n is a natural number chosen from 0, 1 and 2,
   X is chosen from $$\overset{\displaystyle\diagup}{\underset{\displaystyle\diagdown}{C}}=O, \quad \text{or} \quad \overset{\displaystyle\diagup}{\underset{\displaystyle\diagdown}{S}}\overset{\displaystyle=O}{\underset{\displaystyle=O}{}},$$

Ar is a phenyl substituted at para position by

[Structure: 2-methylthiazol-4-yl group]

said compound corresponding to formula (Ic):

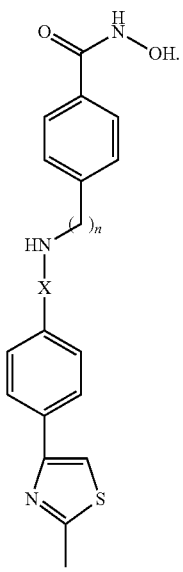

and in a more particular embodiment, embodiment, compounds
wherein either n is 1 and X is

said compound corresponding to formula (Ic1),
or wherein n is 0 and X is

said compound corresponding to formula (Ic2),

The present invention also relates to a compound of formula (I') for its use as a pharmaceutical drug.

In a particular embodiment the present invention concerns a compound of formula (I') for its use as a pharmaceutical drug for treating, inhibiting or preventing a parasitic disease, preferably a protozoan parasitic disease chosen from toxoplasmosis, leishmaniasis, trypanosomiasis, in a mammalian subject, including human, cat or dog.

In one embodiment, the present invention concerns a compound of formula (I') according to any of the above embodiments, for its use as a pharmaceutical drug, in particular for treating, inhibiting or preventing a parasitic disease, preferably a protozoan parasitic disease chosen from toxoplasmosis, leishmaniasis, trypanosomiasis, in a mammalian subject, including human, cat or dog.

In another particular embodiment the present invention concerns a compound of formula (I') for its use as a pharmaceutical drug for treating, inhibiting or preventing a parasitic disease, preferably a protozoan parasitic disease chosen from toxoplasmosis, leishmaniasis, babesiosis, trypanosomiasis, in a mammalian subject, including human, cat or dog.

In a more particular embodiment, the present invention concerns a compound of formula (I') for its use as a pharmaceutical drug, for treating, inhibiting or preventing a parasitic disease, wherein the parasitic disease is caused by a protozoan parasite of the family of the Trypanosomatidae selected from the genus *Trypanosoma* or the genus *Leishmania*, or the parasite *Toxoplasma gondii*.

In another embodiment, the present invention concerns a compound of formula (I') for its use as a pharmaceutical drug, for treating, inhibiting or preventing a parasitic disease, wherein the parasitic disease is caused by a protozoan pyroplasm of the family *Babesia* selected from *Babesia microti* and *Babesia divergens*.

In a particular embodiment the present invention relates to a compound of formula (Ia1), (Ib1), or (Ic1) for its use according as a pharmaceutical drug for treating toxoplasmosis.

In another embodiment, the present invention relates to a compound of formula (Ia1), (Ib1), or (Ic1) for its use according to any one of the previous embodiments, as a pharmaceutical drug for treating babesiosis or piroplasmosis.

In one embodiment, the present invention concerns a compound of formula (I) or (I'), for its use as a pharmaceutical drug for treating, inhibiting or preventing a parasitic disease, preferably a protozoan parasitic disease in a drug-resistant subject.

In this embodiment, a compound of formula (I) or (I'), for its use as a pharmaceutical drug for treating, inhibiting or preventing a parasitic disease, preferably a protozoan parasitic disease in a drug-resistant subject, is a compound selected from the group consisting in (Ia1), (Ia2), (Ib1), (Ib2), (Ib3), (Ib4), (Ic1) and (Ic2); it can be compound (Ia1), (Ia2), (Ib1), (Ib2), (Ib3), (Ib4), (Ic1), or (Ic2), alone or in combination with a conventional anti-parasitic compound selected from the group comprising: miltefosin, antimony based drugs, like meglumine antimoniate or sodium stibogluconate, amphotericin B, benzimidazol, nifurtimox, paromomycin, pentamidin and its derivatives, arsenic derivatives, melarsoprol and difluoromethylornithin, clindamycin, quinine, atovaquone, azithromycin.

In a particular embodiment drug resistant subjects or patients are patients resistant to one or several drugs selected from anti-parasitic drugs, in particular a drug selected from miltefosin, meglumine, antimoniate, sodium stibogluconate, amphotericin B, benzimidazol, nifurtimox, paromomycin, pentamidin melarsoprol, difluoromethylornithin, or a combination thereof and more particularly a drug selected from meglumine antimoniate or sodium stibogluconate, amphotericin B, benzimidazol, nifurtimox, paromomycin, pentamidin and its derivatives, arsenic derivatives, melarsoprol and difluoromethylomithin, clindamycin, quinine, atovaquone, azithromycin.

In a particular embodiment the present invention relates to a compound of formula (Ia1), (Ib1), or (Ic1) for its use according as a pharmaceutical drug for treating toxoplasmosis in drug resistant subjects.

In another embodiment, the present invention relates to a compound of formula (Ia1), (Ib1), or (Ic1) for its use according to the invention, as a pharmaceutical drug for treating babesiosis or piroplasmosis in drug resistant subjects.

An object of the present invention concerns a pharmaceutical composition comprising a compound of formula (I') as defined above or a pharmaceutically acceptable salt thereof, and a pharmaceutical acceptable excipient.

Another object of the present invention concerns a pharmaceutical composition comprising a compound of formula (Ia1), (Ib1), or (Ic1) or a pharmaceutically acceptable salt thereof and a pharmaceutical acceptable excipient.

Another object of the present invention is a pharmaceutical composition comprising:
- a compound of formula (I') according to the invention, or a pharmaceutically acceptable salt thereof, and
- at least one anti-parasitic compound, selected from the group comprising: miltefosin, antimony based drugs, like meglumine antimoniate or sodium stibogluconate, amphotericin B, benzimidazol, nifurtimox, paromomycin, pentamidin and its derivatives, arsenic derivatives, melarsoprol and difluoromethylornithin.

Still another object of the present invention relates to a combination of at least one of any of the compound selected from compound (I), (I'), (Ia1), (Ib1), or (Ic1) or a pharmaceutically acceptable salt with at least one anti-parasitic compound, selected from the group comprising: miltefosin, antimony based drugs, like meglumine antimoniate or sodium stibogluconate, amphotericin B, benzimidazol, nifurtimox, paromomycin, pentamidin and its derivatives, arsenic derivatives, melarsoprol and difluoromethylornithin.

In a particular embodiment the present invention concerns a combination of compound (I') or (Ia1), with one anti-parasitic compound, selected from miltefosin, meglumine antimoniate, sodium stibogluconate, amphotericin B, benzimidazol, nifurtimox, paromomycin, pentamidin melarsoprol and difluoromethylornithin.

In a more advantageous embodiment the present invention concerns a combination of compound (I') or of (Ia1), with one anti-parasitic compound, selected from miltefosin, meglumine antimoniate, sodium stibogluconate, amphotericin B, benzimidazol, nifurtimox, paromomycin, pentamidin melarsoprol and difluoromethylornithin for its use as a treatment of a parasitic disease chosen from toxoplasmosis, a leishmaniasis or trypanosomiasis, more preferably a disease caused by a protozoan parasite of the family of the Trypanosomatidae selected from the genus *Trypanosoma* or the genus *Leishmania*, or the parasite *Toxoplasma gondii*, in a subject in need thereof, in particular in a drug-resistant subject, comprising administering to said subject, in particular to said drug resistant subject, at least a therapeutically effective amount of a said combination.

In another embodiment said combination is a combination of compound of formula (I'), preferably a compound of formula (Ia), (Ib), (Ic), more preferably a compound of formula (Ia1), (Ia2), (Ib1), (Ib2), (Ib3), (Ib4), (Ic1), (Ic2) with at least with one anti-parasitic compound, selected from miltefosin, meglumine antimoniate, sodium stibogluconate, amphotericin B, benzimidazol, nifurtimox, paromomycin, pentamidin melarsoprol and difluoromethylornithin for its use as a treatment in a subject, preferably a drug-resistant subject.

The present invention concerns a method for preparing a compound of formula (I'), comprising the following steps:
(i) the reaction between a compound of formula II'

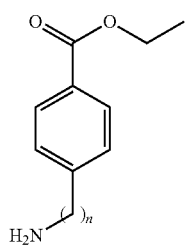

wherein n is a natural number chosen from 0, 1 and 2, with a compound of formula III': Ar—X—Cl, wherein
X is chosen from

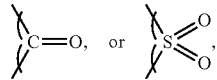

Ar is an aryl, preferably a phenyl, or an arylalkyl, preferably a benzyl, said aryl or arylalkyl being substituted by a halogen, which is a fluor atom, a thiazolyl, or a group chosen from: —$OR_1$ in meta position, —$R_2$—O—$R_1$, wherein $R_1$ represents a $C_1$-$C_8$-alkyl, which is eventually substituted by a halogen, preferably a fluor atom or a thiazolyl, $R_2$ represents a $C_1$-$C_8$ alkylene group eventually substituted by a halogen, preferably a fluor atom or a thiazolyl, to obtain a compound of formula IV'

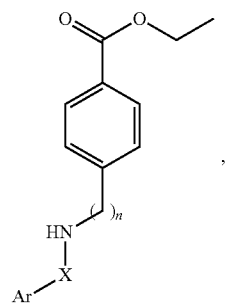

wherein:
n is a natural number chosen from 0, 1 and 2,
X is chosen from

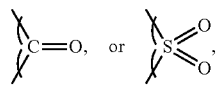

Ar is an aryl, preferably a phenyl, or an arylalkyl, preferably a benzyl, said aryl or arylalkyl being substituted by a halogen, which is a fluor atom, a thiazolyl, or a group chosen from: —$OR_1$ in meta position, —$R_2$—O—$R_1$, wherein $R_1$ represents a $C_1$-$C_8$-alkyl, which is eventually substituted by a halogen, preferably a fluor atom or a thiazolyl, $R_2$ represents a $C_1$-$C_8$ alkylene group eventually substituted by a halogen, preferably a fluor atom or a thiazolyl, (ii) the reaction between the compound of formula IV' and a base to obtain a compound of formula V',

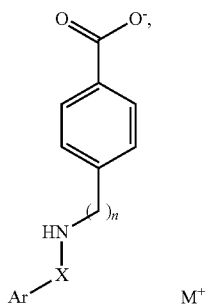

wherein n, X and Ar respectively has the same definition of that for formula IV', said compound of formula V' is eventually acidified, and M⁺ represents a metallic cation, preferably $Na^+$, $K^+$, or $Li^+$;

(iii) the reaction between the compound of formula V' and hydroxylamine to obtain the compound of formula (I').

The present invention is illustrated, but is not limited to, by the following figures and examples.

Document US2003/013757 A1, discloses a compound of formula:

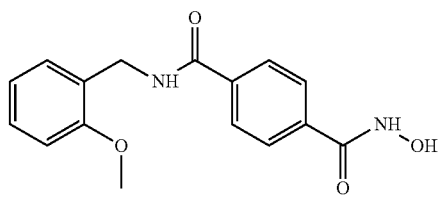 [SMILES: COc1ccccc1CNC(=O)c1ccc(C(=O)NO)cc1]

hereafter named D16.

FIG. 1 illustrates inhibitory activity of compounds (Ia1), (Ia2), (Ib1), (Ib2), (Ib3), (Ib4), (Ic1), (Ic2) and hydroxybenzamide (named also ST3 in the present invention) for *T. gondii* proliferation in human foreskin fibroblasts. X-axis corresponds to Log of concentration of compounds in μM. Y-axis corresponds to parasite growth inhibition percent.

EXAMPLES

Figure 1:
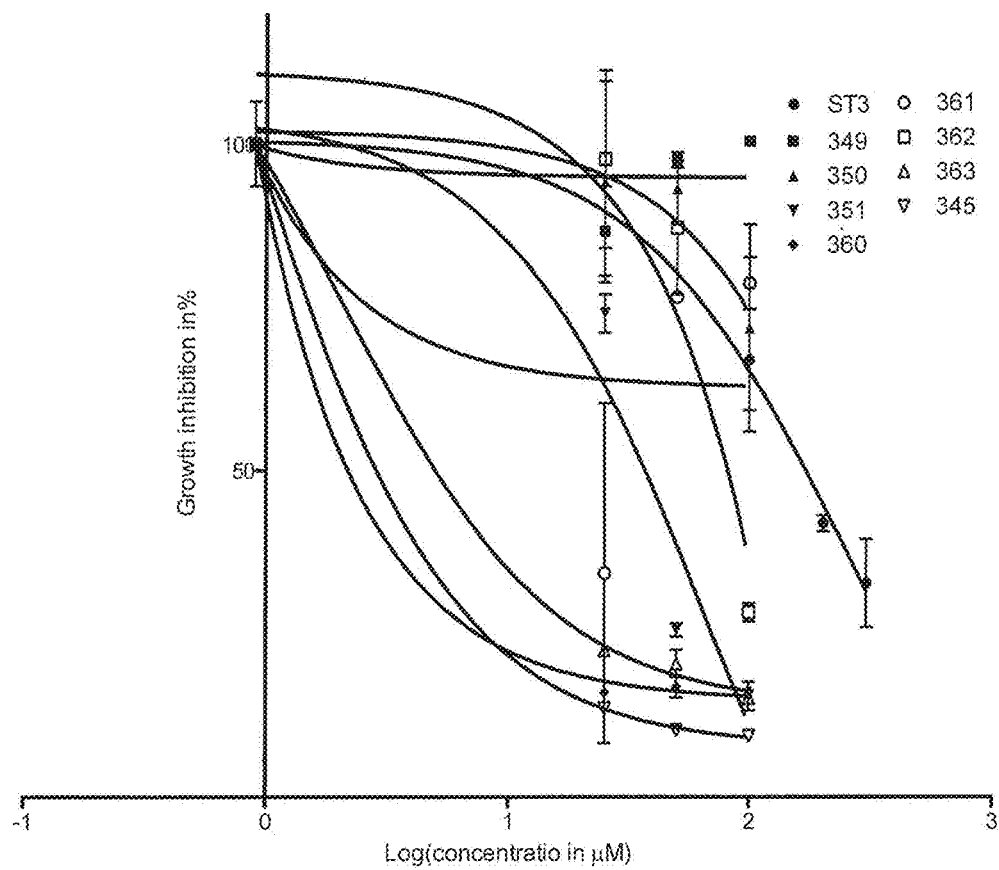

I. Synthesis of a Compound of Formula (I) or (I')

A compound of formula (I) is synthesized according to following steps:

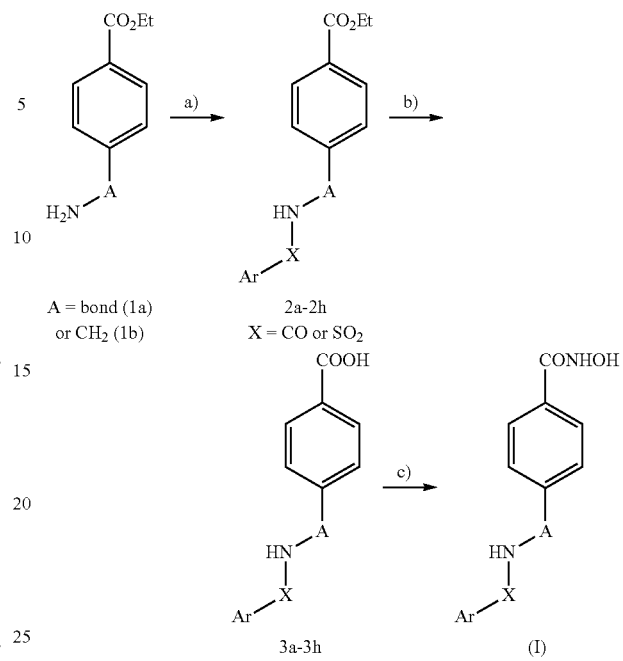

A = bond (1a) or $CH_2$ (1b)

2a-2h
X = CO or $SO_2$ 3a-3h                    (I)

Reagents and conditions: (a) Ar—X—Cl, $NEt_3$, DCM (dichloromethane); (b) LiOH 3 eq., THF(tetrahydrofuran)/H2O 40° C. overnight; (c) (i) Cl—$CO_2Et$, NMM(N-methylmorpholine), DMF(dimethylformamide), (ii) $NH_2OH$, MeOH.

General Procedure for 2a-2h:

Amine derivative 1a or 1b (1 eq.) was dissolved in dry DCM (0.2M). Triethylamine (3 eq.) and the acid chloride or sulfonyl chloride (1 eq.) were added successively and the reaction mixture was heated at 40° C. After the reaction was complete (TLC control), the reaction mixture was concentrated. The residue was taken up with EtOAc and the organic phase was washed with a solution of 1M HCl, a saturated solution of $NaHCO_3$ and brine, dried over $Na_2SO_4$, filtrated and concentrated to afford 2a-2h. The products were used such as in the next step.

General Procedure for 3a-3h:

Derivative 2a-2h (1 eq.) was dissolved in THF (3 ml). A solution of LiOH (3 eq.) in 3 ml of water was added and the reaction mixture was heated at 40° C. overnight. The reaction mixture was concentrated. The residue was taken up with 30 ml of water and the aqueous phase was washed with 20 ml of EtOAc, then the aqueous phase was acidified to pH 2 with a solution of 1M HCl. The aqueous phase was extracted with 3*20 ml of EtOAc. The organic phases were combined and dried over $Na_2SO_4$, filtrated and concentrated to afford 3a-3h. The products were used such as in the next step.

General Procedure for Compound of Formula (I) or (I'):

Derivative of formula (I) (1 eq.) was dissolved in dry DMF (5 ml). Ethyl chloroformate (1.2 eq.) and N-methylmorpholine (1.3 eq.) were added successively at 0° C. After 10 mn, a solution of hydroxylamine (2 eq.) in MeOH (10 ml) was added and the reaction mixture was warm up to room temperature and let overnight. The reaction mixture was concentrated. The residue was taken up with EtOAc and the organic phase was washed with a saturated solution of $NaHCO_3$ and brine, dried over $Na_2SO_4$, filtrated and concentrated. The crude products were purified by flash chromatography to afford a compound of formula (I).

Compound of formula (Ib1): ¹H NMR (200 MHz, DMSO-d6) δ 11.17 (s, 1H), 9.19 (t, J=4.0 Hz, 1H), 9.00 (s, 1H), 7.70 (m, 4H), 7.56 (m, 1H), 7.39 (m, 3H), 4.51 (d, J=4.0 Hz, 2H). HPLC rt=3.356 min. (purity 100%). The calculated MS ESI+H⁺ is 289.28 and experimentally obtained is 289.10.

Compound of formula (Ib2): ¹H NMR (200 MHz, DMSO-d6) δ 10.40 (s br, 1H), 7.75 (m, 6H), 7.58 (m, 1H), 7.45 (m, 1H). HPLC rt=3.553 min. (purity 98%). The calculated MS ESI+H⁺ is 275.25 and experimentally obtained is 275.10.

Compound of formula (Ib3): ¹H NMR (200 MHz, DMSO-d6) δ 11.17 (s, 1H), 9.02 (s, 1H), 8.37 (s, 1H), 7.60 (m, 4H), 7.50 (m, 2H), 7.29 (d, J=5.6 Hz, 2H), 4.07 (s, 2H). HPLC rt=3.635 min. (purity 97%). The calculated MS ESI+H⁺ is 325.30 and experimentally obtained is 325.10.

Compound of formula (Ib4): ¹H NMR (200 MHz, DMSO-d6) δ 11.07 (s, 1H), 10.75 (s, 1H), 8.95 (s, 1H), 7.55 (m, 5H), 7.48 (m, 1H), 7.15 (d, J=5.8 Hz, 2H). HPLC rt=3.531 min. (purity 100%). The calculated MS ESI+H⁺ is 311.31 and experimentally obtained is 311.10.

Compound of formula (Ic1): ¹H NMR (200 MHz, DMSO-d6) δ 11.18 (s, 1H), 9.13 (t, J=4.0 Hz, 1H), 9.01 (s, 1H), 8.09 (s, 1H), 7.98 (d, J=Hz, 2H), 7.95 (d, J=Hz, 2H), 7.70 (d, J=5.8 Hz, 2H), 7.38 (d, J=5.8 Hz, 2H), 4.52 (d, J=4.0 Hz, 2H), 2.73 (s, 3H). HPLC rt=3.828 min. (purity 96%). The calculated MS ESI+H⁺ is 368.43 and experimentally obtained is 368.10.

Compound of formula (Ic2): ¹H NMR (200 MHz, DMSO-d6) δ 11.13 (s, 1H), 10.46 (s, 1H), 8.95 (s, 1H), 8.14 (s, 1H), 8.10 (d, J=4.2 Hz, 2H), 8.03 (d, J=4.2 Hz, 2H), 7.87 (d, J=4.4 Hz, 2H), 7.76 (d, J=4.4 Hz, 2H), 2.75 (s, 3H). HPLC rt=3.984 min. (purity 100%). The calculated MS ESI+H⁺ is 354.40 and experimentally obtained is 354.10.

Compound of formula (Ia2): ¹H NMR (200 MHz, DMSO-d6) δ 11.17 (s, 1H), 8.99 (s, 1H), 8.58 (t, J=4.0 Hz, 1H), 7.67 (d, J=5.4 Hz, 2H), 7.29 (d, J=5.4 Hz, 2H), 7.19 (t, J=5.8 Hz, 1H), 6.80 (m, 3H), 4.30 (d, J=4.0 Hz, 2H), 3.73 (s, 3H), 3.45 (s, 2H). HPLC rt=3.370 min. (purity 100%). The calculated MS ESI+H⁺ is 315.34 and experimentally obtained is 315.10.

Compound of formula (Ia1): ¹H NMR (200 MHz, DMSO-d6) δ 11.09 (s, 1H), 10.35 (s, 1H), 8.93 (s, 1H), 7.70 (d, J=5.8 Hz, 2H), 7.64 (d, J=5.8 Hz, 2H), 7.22 (t, J=5.4 Hz, 1H), 6.89 (m, 2H), 6.82 (d, J=4.8 Hz, 1H), 3.74 (s, 3H), 3.63 (s, 2H). HPLC rt=3.618 min. (purity 99%). The calculated MS ESI+H⁺ is 301.32 and experimentally obtained is 301.10.

II. Inhibition of Histone Deacetylase Activity Derived from HELA Nuclear Extract, of Some Recombinant Proteins and of *T. gondii* Total Protein Extract HDAC inhibitory activity was determined by a fluorimetric HDAC assay kit (Active-motif, Belgium), according to manufacturer's instructions. Briefly, 30 μL of HeLa nuclear extract were mixed with 5 μL of 10× compound to be tested and 10 μL of assay buffer. Fluorogenic substrate (10 μL) was added, reaction was allowed to proceed for 30 min at room temperature, then stopped by the addition of a developer containing Tichostatin A. Fluorescence was monitored after 30 min at excitation and emission wavelengths of 360 and 460 nm, respectively. HDAC inhibitory activity of the compounds of formula (Ia1), (Ia2), (Ib1), (Ib2), (Ib3), (Ib4), (Ic1), (Ic2) was assayed and compared to that of hydroxybenzamide, which is an anti-parasitic compound described in PCT/EP2011/004055, to suberoylanilide hydroxamic acid (SAHA) a known inhibitor of HDAC activity, and to D16. The results are exposed in Table 1.

TABLE 1

| Compounds | cLogP | Structure | HELA Nuclear extracts IC50 in nM |
|---|---|---|---|
| SAHA (suberoylanilide hydroxamic acid) | ND | 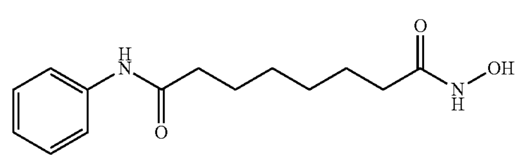 [SMILES: O=C(CCCCCCC(=O)Nc1ccccc1)NO] | 2100 +/− 200 |
| ST3 (hydroxybenzamide) | 0.855 | 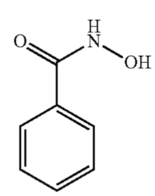 | 7865 +/− 908 |

TABLE 1-continued

| Compounds | cLogP | Structure | HELA Nuclear extracts IC50 in nM |
|---|---|---|---|
| Compound (Ib1), named also 345 | 1.545 | 4-(hydroxycarbamoyl)benzyl 3-fluorobenzamide structure | 866 +/− 400 |
| Compound (Ib2), named also 349 | 1.844 | N-hydroxy-4-(3-fluorobenzamido)benzamide structure | 633 +/− 41 |
| Compound (Ib3), named also 350 | 1.420 | 4-(hydroxycarbamoyl)benzyl 3-fluorobenzenesulfonamide structure | 8611 +/− 1540 |
| Compound (Ib4) named also 351 | 1.719 | N-hydroxy-4-((3-fluorophenyl)sulfonamido)benzamide structure | 881 +/− 83 |

TABLE 1-continued

| Compounds | cLogP | Structure | HELA Nuclear extracts IC50 in nM |
|---|---|---|---|
| Compound (Ic1), named also 360 | 1.724 | 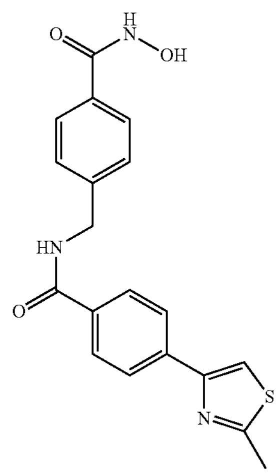 [SMILES: Cc1nc(-c2ccc(C(=O)NCc3ccc(C(=O)NO)cc3)cc2)cs1] | 399 +/− 137 |
| Compound (Ic2), named also 361 | 2.022 | 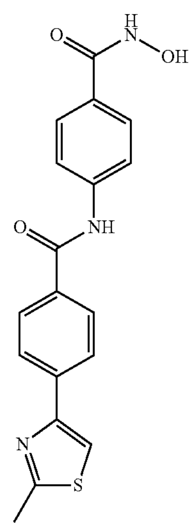 [SMILES: Cc1nc(-c2ccc(C(=O)Nc3ccc(C(=O)NO)cc3)cc2)cs1] | 1825* |
| Compound (Ia2), named also 362 | 1.438 | 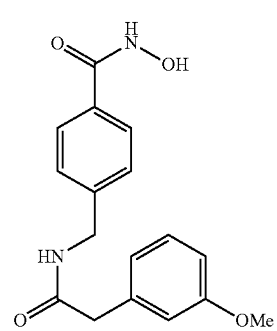 [SMILES: COc1cccc(CC(=O)NCc2ccc(C(=O)NO)cc2)c1] | 518 +/− 146 |

TABLE 1-continued

| Compounds | cLogP | Structure | HELA Nuclear extracts IC50 in nM |
|---|---|---|---|
| Compound (Ia1), named also 363 | 1.829 | 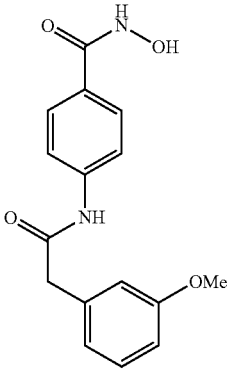 [SMILES: COc1cccc(CC(=O)Nc2ccc(C(=O)NO)cc2)c1] | 85 +/− 35 |
| Compound D16 | ND | 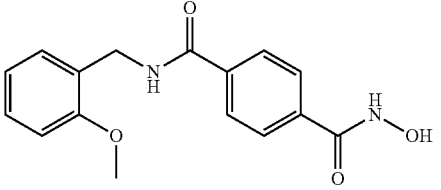 [SMILES: COc1ccccc1CNC(=O)c1ccc(C(=O)NO)cc1] | 7735 +/− 1300 |

ND: not determined
cLogP is the calculated LogP
Hela nuclear extracts IC50 represents the inhibitory activity of a compound.

The results of Table 1 show that the 9 compounds tested represent HDAC inhibitory activity against HeLa cell nuclear extract, which contains primarily HDACs 1,2,6,8. HDAC inhibitory activity of these compounds, which is from about 1 µM for the less active compounds (ST3, compound 350 and compound 361) to 85 nM for the more active ones (compound 363), is in the activity range of well-known HDAC inhibitors and is higher than the inhibitory activity of SAHA that has been shown to be in the micromolar range of activity (1300 nM) (Jiao et al., Eur. J Med. Chem. 2009. 44:4470-4476), $IC_{50}$ of 2000 nM in our experiment (Table 1). The inhibitory activity of compound D16 in HELA Nuclear extracts was the lowest as compared to other compounds in Table 1, with an IC50 value of 7735+/−1300 nM.

Figure 2:
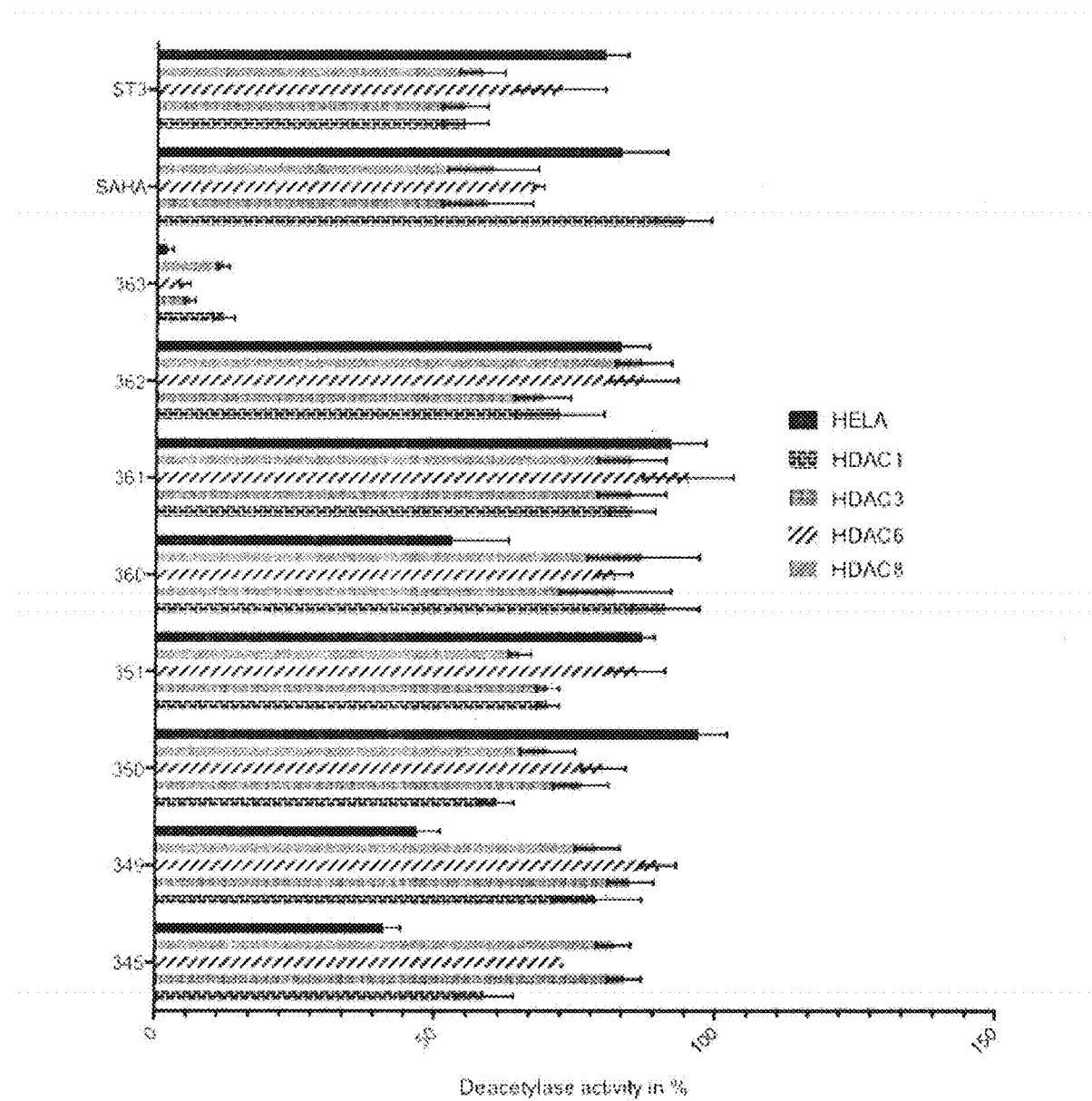
FIG. 2 illustrates the capacity of the different compounds of 600 nM to inhibit HDAC activity from HELA nuclear extract and from HDAC-recombinant proteins (HDAC 1, HDAC 3, HDAC 6, HDAC 8).

The data of FIG. 2 show that the compound 363 is the most potent inhibitor of the human HDAC activity. The $IC_{50}$ of 363 is of 257+/−50, 160+/−52, 45+/−15 and 863+/−45 nM for recombinant HDAC1, HDAC3, HDAC6 and HDAC 8 respectively. It is a 3 to 100 fold more potent inhibitor for HDAC activity than SAHA ($IC_{50}$ of 627+/−39, 170+/−14, 1573+/−800, 230+/−130 nM for HDAC1, HDAC 3, HDAC6 and HDAC8 respectively).

The $IC_{50}$ of D16 is of more than 10 microM for recombinant HDAC1 and of 198+/−40 nM for recombinant HDAC6.

Figure 3:
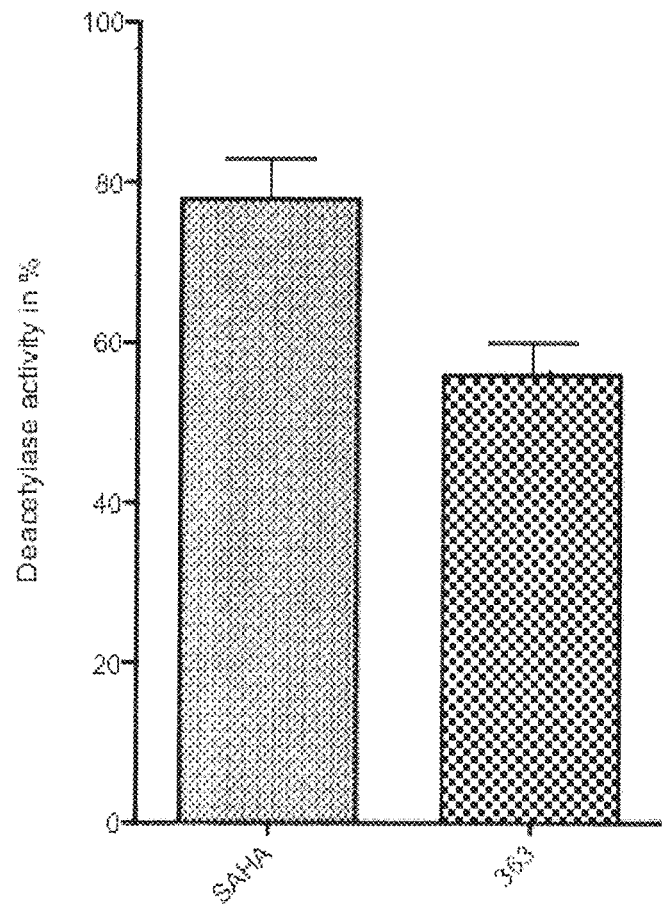
FIG. 3 illustrates the inhibitory effect of 125 nM of compound 363 on deacetylase activity measured in total protein extracts of *T. gondii*.

As showed in FIG. 3, at 125 nM the compound 363 expresses a strong inhibitory effect on deacetylase activity measured in total protein extracts of T. gondii. It inhibits 44% of the T. gondii deacetylase activity whereas SAHA inhibit only 22% of this activity. This suggests that the compounds express broad inhibitory activity against both human and protozoan histone deacetylase activity.

The compound (I) or (I') according to the invention have a strong and more specific inhibitory effect on Histone deacetylase activity, advantageously on Histone deacetylase 1 and 6 activity.

III. Inhibition of T. gondii and Leishmania Proliferation

The potential of aforementioned 9 compounds to inhibit the proliferation of T. gondii and Leishmania was also investigated.

To assess the drug activity on toxoplasma proliferation, human foreskin fibroblasts (HFF) were infected with GFP expressing parasites for 30 mns (Striepen et al., Mol Biochem Parasitol. 1998, 92(2):325-38). Cells were then washed and drugs added at various concentrations ranging from 0.1 to 10 uM. After 24 h, cells were washed and fixed (PBS-formaldehyde 2%) and nucleus stained with Hoechst 33258 (2 µg/ml). The number of infected cells i.e cells harbouring a parasitophorous vacuole and the number of parasites per vacuole were determined using an Olympus ScanR microscope (Olympus).

Leishmanicidal activity was determined according to a previously published protocol that used Leishmania infantum luciferase expressing strain (MHOM/MA/ITMAP269) (Sereno D & Lemesre J L., Antimicrob Agents Chemother 1997, 41(5): 972-976).

Antiparasitic activity of a compound is represented by $IC_{50}$, which is calculated with Prism software (Prism4 for MacOSX Version 5.0b, December 2008). The cytotoxicity of a compound against the host cells of L. infantum and T. gondii, such as THP-1 or HFF cells, was determined with a MTT assay, according to previously described protocol (Sereno et al., Antimicrob Agents Chemother. 2001, 45(4): 1168-73). THP-1 is derived from the peripheral blood of a 1 year old human male with acute monocytic leukemia.

Antiparasitic activity and cytotoxicity of these compounds are summarized in FIG. 1 and table 2.

TABLE 2

| Compound | cLogP | L. infantum IC50 | T. gondi IC50 | HFF LD$_{50}$ | IS | THP-1 LD$_{50}$ | IS |
|---|---|---|---|---|---|---|---|
| SAHA | | >100 | ND | ND | ND | >200 | ND |
| ST3 | 0.855 | 29.3 +/− 14.4 | >50 | >400 | ND | 271.0 +/_30.0 | ND |
| 345 | 1.545 | 27.2 +/− 2.5 | 5.0 +/− 1.0 | 58.3 +/− 1.2 | 11.6 | 1.7. +/− 0.5 | 0.3 |
| 349 | 1.844 | >60.0 | >50 | >400 | ND | 264 +/− 8.0 | ND |
| 350 | 1.420 | >60.0 | 40.0 +/10.0 | 300.0 +/− 50.0 | 7.5 | >400 | 10 |
| 351 | 1.719 | >60.0 | 50 | 116.5 +/− 35 | 2.3 | 76.5-17.9-5.8 | 1.53 |
| 360 | 1.724 | >60.0 | 4.9 +/− 0.15 | 22.6 +/− 9.5 | 4.5 | 2.2 +/− 0.5 | 0.4 |
| 361 | 2.022 | >60.0 | >10 | 25.0 +/− 4.0 | 1.5 | >400 | 25 |
| 362 | 1.438 | >60.0 | 52.5 +/− 10.4 | >400 | >8 | 30.5 +/− 3.0 | 0.5 |
| 363 | 1.829 | >60.0 | 0.35 +/− 0.05 | 105 +/− 10.5 | 300 | 3.6 +/− 0.5 | 10.3 |

Antiparasitic activity: IC50 in μM. Cytotoxicity: DL50 in μM. IS: Selectivity index: LD50 (HFF or THP-1)/IC50 T. gondii.

Of the 8 compounds synthesized of the present invention, 3 compounds (compounds 345, 360, 363) inhibit the proliferation of the T. gondii at concentrations below 10 μM. Interestingly, all these 3 compounds are also the better HDAC inhibitor among 9 tested compounds (IC50 of 1.7 μM, 2.2 M and 3.6 μM respectively). The compound 345 is the sole compound having both anti-leishmanial and anti-toxoplasma activity (Table 2). ST3 is another compound also presenting anti-leishmanial activity. Amongst the 9 compounds synthetized in Table 2 which have an IC50 value ranging from more than 60 μM to less than 1 μM, the compound 363 is the most selective for the intracellular proliferative stage of T. gondii. The difference between the selectivity index of 300 in HFF cells and 10 in THP-1 cells can be explained by the fact that THP-1 cell line is known to be susceptible to hydroxamate derivatives and therefore might not be ideal to evaluate the cytotoxicity of hydroxamate derivatives against host cells (Sung et al., Apoptosis. 2010, 15(10):1256-69). The HEPG2 cell line is considered as a model system for the studies of liver metabolism and toxicity of xenobiotics. An IC$_{50}$ superior to 15 μM for 363 and a calculated index of selectivity of 42, confirm the high selectivity of 363 for T. gondii tachyzoïtes.
The present results demonstrate an inhibitory activity of the compound according to the invention on Toxoplasma or on Leishmania proliferation.

IV. Inhibition of RH-YFP Type I or Type II Prugniaud Toxoplasma Proliferation
To compare the activity of compounds according to the invention to that of prior art on toxoplasma proliferation, human foreskin fibroblasts (HFF) were plated in 96-wells plate (10 000 cells per well). Twenty-four hours later, cells were infected with 40 000 parasites, either RH-YFP type I or type II Prugniaud parasites or tachyzoites (kindly provided by B. Striepen, Athens) for one hour. Cells were then washed and drugs (compound D16 of formula

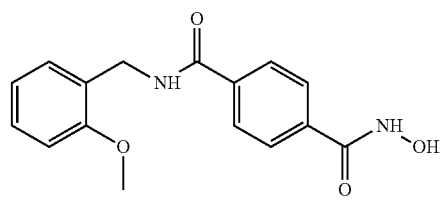 [SMILES: COc1ccccc1CNC(=O)c1ccc(C(=O)NO)cc1]

Figure 4:
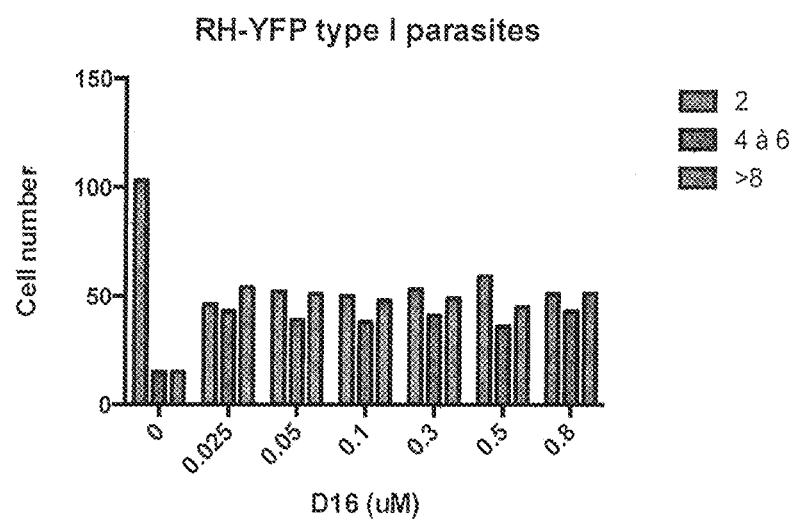
FIG. 4 illustrates the lack of inhibitory effect of D16 on type I RH-YFP proliferation.
Figure 5:
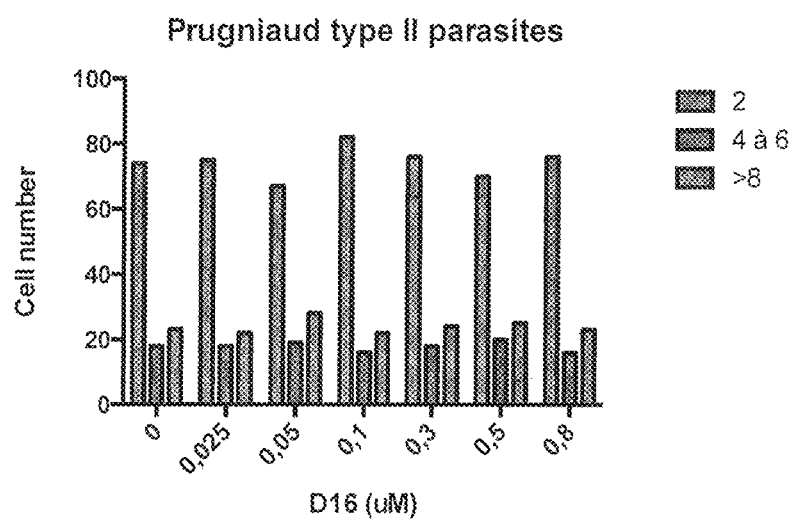
FIG. 5 illustrates the lack of inhibitory effect of D16 on type II Prugniaud *T. gondii* proliferation.
Figure 6:
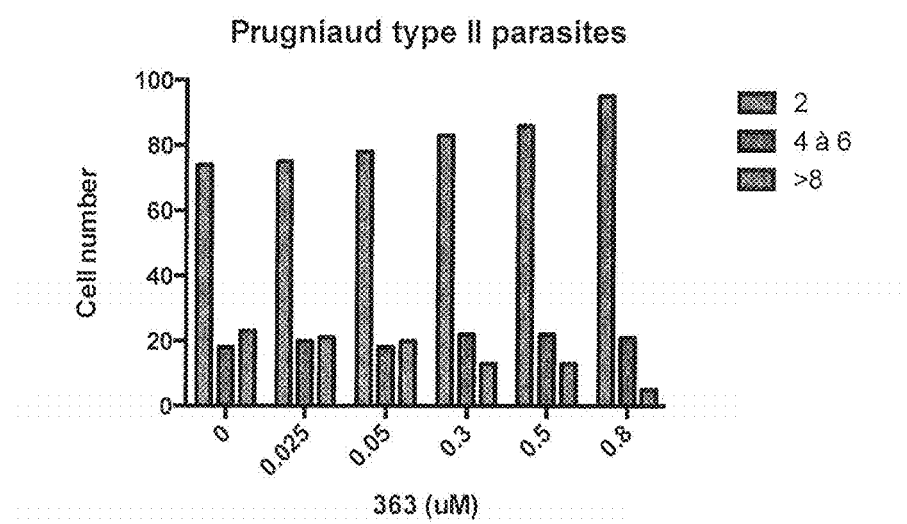
FIG. 6 illustrates the potent inhibitory effect of compound 363 on type II Prugniaud *T. gondii* proliferation.

(FIG. 4 and FIG. 5) or compound according to the invention (363) (FIG. 6) added at various concentrations ranging from 0.025 to 0.8 uM. After 24 h, cells were washed and fixed (PBS-formaldehyde 2%) and nucleus stained with Hoechst 33258 (2 μg/ml). The number of infected cells i.e. cells harbouring a parasitophorous vacuole and the number of parasites per vacuole was determined using an Olympus ScanR microscope (Olympus).
As shown in FIG. 4, D16 has no inhibitory activity on type I RH-YFP parasites proliferation.
As shown in FIG. 5, D16 has no inhibitory activity on type II Prugniaud parasites proliferation.
As shown in FIG. 6, compound according to the invention 363 has a potent inhibitory activity on type II Prugniaud parasites proliferation.
The present results demonstrate an inhibitory activity of the compound according to the invention on Toxoplasma type I and type II parasites proliferation.
The present results also demonstrated an inhibitory activity of the compound according to the invention on Babesia proliferation, in particular the IC50 calculated for compound 363 was about 1 microM.
The compound according to the invention has an anti-Babesia activity.

The invention claimed is:
1. A pharmaceutical composition comprising:
a compound of formula (I'):

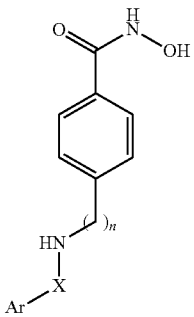

wherein:
n is 0, 1 or 2,
X is

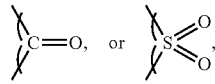

Ar is a benzyl substituted at the meta position by a $C_1$ to $C_8$ alkoxy group or a pharmaceutically acceptable salt thereof; and at least one anti-parasitic compound, selected from the group consisting of: miltefosin, antimony based drugs, meglumine antimoniate, sodium stibogluconate, amphotericin B, benzimidazol, nifurtimox, paromomycin, pentamidin and its derivatives, arsenic derivatives, melarsoprol and difluoromethylornithin.

2. The pharmaceutical composition according to claim 1, wherein the benzyl is substituted at the meta position by a $C_1$ to $C_4$ alkoxy group.

3. The pharmaceutical composition according to claim 1, wherein in the compound of formula (I') the benzyl is substituted at the meta-position by a methoxy group.

4. The pharmaceutical composition according to claim 3, wherein in the compound of formula (I') either n is 0 and X is

said compound corresponding to formula (Ia1),

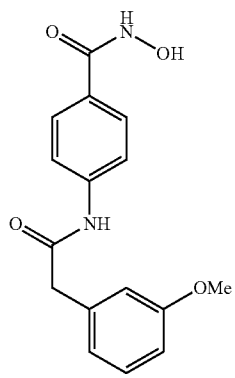 [SMILES: COc1cccc(CC(=O)Nc2ccc(C(=O)NO)cc2)c1]

or wherein n is 1 and X is

said compound corresponding to formula (Ia2)

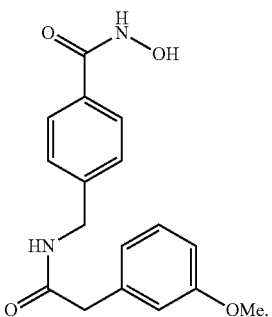 [SMILES: COc1cccc(CC(=O)NCc2ccc(C(=O)NO)cc2)c1]

5. A method for treating a parasitic disease in a mammalian subject, comprising applying to the subject an effective amount of the pharmaceutical composition of claim 1.

6. The method of claim 5, wherein the parasitic disease is caused by a protozoan parasite of the family of the Trypanosomatidae selected from the genus *Trypanosoma* or the genus *Leishmania*, or the parasite *Toxoplasma gondii*.

7. A method for treating toxoplasmosis in a mammalian subject, comprising applying to the subject an effective amount of the pharmaceutical composition.

8. The pharmaceutical composition according to claim 1 comprising a pharmaceutical acceptable excipient.

9. The method of claim 5, wherein the mammalian subject is a human, dog or cat.

10. The method of claim 5, wherein in the compound of formula (I') in the pharmaceutical composition Ar is a benzyl substituted at the meta position by a $C_1$ to $C_4$ alkoxy group.

11. The method of claim 10, wherein Ar is a benzyl substituted at the meta-position by a methoxy group.

* * * * *